(12) United States Patent
Soltis et al.

(10) Patent No.: US 10,894,162 B2
(45) Date of Patent: Jan. 19, 2021

(54) DELIVERY DEVICES AND METHODS FOR LEADLESS CARDIAC DEVICES

(71) Applicant: CARDIAC PACEMAKERS, INC., St. Paul, MN (US)

(72) Inventors: Brian Soltis, St. Paul, MN (US); Ronald W. Kunkel, Jim Falls, WI (US); Kurt G. Koubal, Mound, MN (US); James P. Goodman, Shorewood, MN (US)

(73) Assignee: CARDIAC PACEMAKERS, INC., St. Paul, MN (US)

( * ) Notice: Subject to any disclaimer, the term of this patent is extended or adjusted under 35 U.S.C. 154(b) by 374 days.

(21) Appl. No.: 15/852,384

(22) Filed: Dec. 22, 2017

(65) Prior Publication Data

US 2018/0178006 A1 Jun. 28, 2018

Related U.S. Application Data

(60) Provisional application No. 62/439,261, filed on Dec. 27, 2016.

(51) Int. Cl.
*A61N 1/362* (2006.01)
*A61N 1/05* (2006.01)
(Continued)

(52) U.S. Cl.
CPC .............. *A61N 1/362* (2013.01); *A61N 1/059* (2013.01); *A61N 1/372* (2013.01); *A61N 1/3756* (2013.01);
(Continued)

(58) Field of Classification Search
CPC ...... A61N 1/056; A61N 1/057; A61N 1/0587; A61N 1/059; A61N 1/362; A61N 1/372;
(Continued)

(56) References Cited

U.S. PATENT DOCUMENTS 4,301,815 A 11/1981 Doring
5,807,399 A 9/1998 Laske et al.
(Continued)

FOREIGN PATENT DOCUMENTS

EP 2818201 B1 7/2016
EP 2658599 B1 10/2016
(Continued)

OTHER PUBLICATIONS

International Search Report and Written Opinion dated Jun. 25, 2018 for International Application No. PCT/US2017/068157.

*Primary Examiner* — Robert A Lynch
(74) *Attorney, Agent, or Firm* — Seager Tufte & Wickhem LLP

(57) ABSTRACT

Delivery devices, systems, and methods for delivering implantable leadless pacing devices are disclosed. An example delivery device may include an intermediate tubular member and an inner tubular member slidably disposed within a lumen of the intermediate tubular member. A distal holding section may extend distally of a distal end of the intermediate tubular member and define a cavity therein for receiving an implantable leadless pacing device. At least a portion of the lumen of the inner tubular member may be bifurcated to form a first lumen and a second lumen. The first lumen may be configured to receive a first portion of a tether and the second lumen may be configured to receive a second portion of the tether

6 Claims, 10 Drawing Sheets

(51) Int. Cl.
*A61N 1/375* (2006.01)
*A61N 1/372* (2006.01)
*A61M 25/00* (2006.01)
*A61M 25/01* (2006.01)

(52) U.S. Cl.
CPC ....... *A61M 25/003* (2013.01); *A61M 25/0082* (2013.01); *A61M 25/0097* (2013.01); *A61M 25/0102* (2013.01); *A61M 25/0136* (2013.01); *A61M 25/0147* (2013.01); *A61M 2025/0004* (2013.01); *A61N 1/37205* (2013.01); *A61N 1/37518* (2017.08)

(58) Field of Classification Search
CPC .............. A61N 1/37205; A61N 1/3756; A61N 2001/0578; A61N 2001/058; A61M 25/0026; A61M 25/003; A61M 25/0097; A61M 25/01; A61M 25/0102; A61M 25/0147; A61M 2025/0004
See application file for complete search history.

(56) References Cited

U.S. PATENT DOCUMENTS

| | | |
|---|---|---|
| 5,908,381 A | 6/1999 | Aznoian et al. |
| 6,181,973 B1 | 1/2001 | Ceron et al. |
| 6,224,725 B1 | 5/2001 | Glocker |
| 6,395,017 B1 | 5/2002 | Dwyer et al. |
| 6,409,674 B1 | 6/2002 | Brockway et al. |
| 6,497,803 B2 | 12/2002 | Glocker et al. |
| 6,551,477 B2 | 4/2003 | Glocker et al. |
| 6,582,441 B1 | 6/2003 | He et al. |
| 6,638,268 B2 | 10/2003 | Niazi |
| 6,786,918 B1 | 9/2004 | Krivoruchko et al. |
| 7,248,913 B2 | 7/2007 | Hassett |
| 7,321,798 B2 | 1/2008 | Muhlenberg et al. |
| 7,381,216 B2 | 6/2008 | Buzzard et al. |
| 7,499,758 B2 | 3/2009 | Cates et al. |
| 7,509,169 B2 | 3/2009 | Eigler et al. |
| 7,608,099 B2 | 10/2009 | Johnson et al. |
| 7,666,203 B2 | 2/2010 | Chanduszko et al. |
| 7,678,081 B2 | 3/2010 | Whiting et al. |
| 7,799,037 B1 | 9/2010 | He et al. |
| 7,840,281 B2 | 11/2010 | Kveen et al. |
| 7,937,161 B2 | 5/2011 | Hastings et al. |
| 7,993,351 B2 | 8/2011 | Worley et al. |
| 8,002,822 B2 | 8/2011 | Glocker et al. |
| 8,010,209 B2 | 8/2011 | Jacobson |
| 8,103,361 B2 | 1/2012 | Moser |
| 8,185,213 B2 | 5/2012 | Kveen et al. |
| 8,267,987 B2 | 9/2012 | Johnson et al. |
| 8,352,028 B2 | 1/2013 | Wenger |
| 8,364,280 B2 | 1/2013 | Marnfeldt et al. |
| 8,382,813 B2 | 2/2013 | Shumer |
| 8,428,750 B2 | 4/2013 | Kolberg |
| 8,478,431 B2 | 7/2013 | Griswold et al. |
| 8,504,156 B2 | 8/2013 | Bonner et al. |
| 8,527,068 B2 | 9/2013 | Ostroff |
| 8,532,790 B2 | 9/2013 | Griswold |
| 8,548,605 B2 | 10/2013 | Ollivier |
| 8,615,310 B2 | 12/2013 | Khairkhahan et al. |
| 8,634,912 B2 | 1/2014 | Bornzin et al. |
| 8,721,587 B2 | 5/2014 | Berthiaume et al. |
| 8,727,996 B2 | 5/2014 | Allan et al. |
| 8,758,365 B2 | 6/2014 | Bonner et al. |
| 8,855,789 B2 | 10/2014 | Jacobson |
| 8,894,824 B2 | 11/2014 | Glocker et al. |
| 8,903,513 B2 | 12/2014 | Ollivier |
| 8,926,588 B2 | 1/2015 | Berthiaume et al. |
| 8,945,145 B2 | 2/2015 | Tran et al. |
| 8,945,146 B2 | 2/2015 | Steingisser et al. |
| 8,948,883 B2 | 2/2015 | Eggen et al. |
| 8,958,892 B2 | 2/2015 | Khairkhahan et al. |
| 9,020,611 B2 | 4/2015 | Khairkhahan et al. |
| 9,072,872 B2 | 7/2015 | Asleson et al. |
| 9,101,281 B2 | 8/2015 | Reinert et al. |
| 9,119,959 B2 | 9/2015 | Rys et al. |
| 9,126,032 B2 | 9/2015 | Khairkhahan et al. |
| 9,155,882 B2 | 10/2015 | Grubac et al. |
| 9,168,372 B2 | 10/2015 | Fain |
| 9,204,842 B2 | 12/2015 | Mothilal et al. |
| 9,205,225 B2 | 12/2015 | Khairkhahan et al. |
| 9,216,293 B2 | 12/2015 | Berthiaume et al. |
| 9,220,906 B2 | 12/2015 | Griswold et al. |
| 9,238,145 B2 | 1/2016 | Wenzel et al. |
| 9,242,102 B2 | 1/2016 | Khairkhahan et al. |
| 9,272,155 B2 | 3/2016 | Ostroff |
| 9,283,381 B2 | 3/2016 | Grubac et al. |
| 9,283,382 B2 | 3/2016 | Berthiaume et al. |
| 9,283,392 B2 | 3/2016 | Moore et al. |
| 9,308,365 B2 | 4/2016 | Nordstrom et al. |
| 9,308,374 B2 | 4/2016 | Kveen et al. |
| 9,339,197 B2 | 5/2016 | Griswold et al. |
| 9,351,648 B2 | 5/2016 | Mothilal et al. |
| 9,358,387 B2 | 6/2016 | Suwito et al. |
| 9,414,857 B2 | 8/2016 | Wood et al. |
| 9,421,384 B2 | 8/2016 | Taff et al. |
| 9,433,780 B2 | 9/2016 | Regnier et al. |
| 9,446,248 B2 | 9/2016 | Sheldon et al. |
| 9,463,315 B2 | 10/2016 | Bornzin et al. |
| 9,468,773 B1 | 10/2016 | Anderson et al. |
| 9,504,820 B2 | 11/2016 | Bonner et al. |
| 9,511,236 B2 | 12/2016 | Varady et al. |
| 9,517,336 B2 | 12/2016 | Eggen et al. |
| 9,517,337 B2 | 12/2016 | Ollivier |
| 9,526,522 B2 | 12/2016 | Wood et al. |
| 9,526,891 B2 | 12/2016 | Eggen et al. |
| 9,539,423 B2 | 1/2017 | Bonner et al. |
| 9,555,236 B2 | 1/2017 | Regnier et al. |
| 9,579,500 B2 | 2/2017 | Rys et al. |
| 9,610,454 B2 | 4/2017 | Doan et al. |
| 9,623,234 B2 | 4/2017 | Anderson |
| 9,662,487 B2 | 5/2017 | Kveen et al. |
| 9,675,798 B2 | 6/2017 | Grubac et al. |
| 9,717,421 B2 | 8/2017 | Griswold et al. |
| 9,724,507 B2 | 8/2017 | Wood et al. |
| 9,750,931 B2 | 9/2017 | Wood et al. |
| 9,764,139 B2 | 9/2017 | Christensen |
| 9,775,982 B2 | 10/2017 | Grubac et al. |
| 9,808,617 B2 | 11/2017 | Ostroff et al. |
| 9,808,629 B2 | 11/2017 | Steingisser et al. |
| 9,814,896 B2 | 11/2017 | Solem |
| 9,833,625 B2 | 12/2017 | Waldhauser et al. |
| 9,833,626 B2 | 12/2017 | Klimovitch et al. |
| 9,844,659 B2 | 12/2017 | Grubac et al. |
| 9,844,664 B2 | 12/2017 | McEvoy et al. |
| 9,861,815 B2 | 1/2018 | Tran et al. |
| 9,867,982 B2 | 1/2018 | Berthiaume et al. |
| 2003/0078618 A1 | 4/2003 | Fey et al. |
| 2005/0101984 A1 | 5/2005 | Chanduszko et al. |
| 2005/0165472 A1 | 7/2005 | Glocker |
| 2005/0209653 A1 | 9/2005 | Herbert et al. |
| 2005/0267555 A1 | 12/2005 | Marnfeldt et al. |
| 2006/0009737 A1 | 1/2006 | Whiting et al. |
| 2009/0082828 A1 | 3/2009 | Ostroff |
| 2010/0274227 A1 | 10/2010 | Khairkhahan et al. |
| 2011/0112548 A1 | 5/2011 | Fifer et al. |
| 2011/0270339 A1 | 11/2011 | Murray, III et al. |
| 2011/0270340 A1 | 11/2011 | Pellegrini et al. |
| 2012/0095539 A1 | 4/2012 | Khairkhahan et al. |
| 2012/0109148 A1 | 5/2012 | Bonner et al. |
| 2012/0172690 A1 | 7/2012 | Anderson et al. |
| 2012/0172891 A1 | 7/2012 | Lee |
| 2012/0172892 A1 | 7/2012 | Grubac et al. |
| 2013/0012925 A1 | 1/2013 | Berthiaume et al. |
| 2013/0035636 A1 | 2/2013 | Beasley et al. |
| 2013/0103047 A1 | 4/2013 | Steingisser et al. |
| 2013/0253342 A1 | 9/2013 | Griswold et al. |
| 2013/0253346 A1 | 9/2013 | Griswold et al. |
| 2014/0018818 A1 | 1/2014 | Somogyi et al. |
| 2014/0324145 A1 | 10/2014 | Eggen et al. |
| 2014/0378991 A1 | 12/2014 | Ollivier |
| 2015/0039070 A1 | 2/2015 | Kuhn et al. |
| 2015/0045868 A1 | 2/2015 | Bonner et al. |

(56) References Cited

U.S. PATENT DOCUMENTS

| | | |
|---|---|---|
| 2015/0051609 A1 | 2/2015 | Schmidt et al. |
| 2015/0051610 A1 | 2/2015 | Schmidt et al. |
| 2015/0051611 A1 | 2/2015 | Schmidt et al. |
| 2015/0051612 A1 | 2/2015 | Schmidt et al. |
| 2015/0051613 A1 | 2/2015 | Schmidt et al. |
| 2015/0051615 A1 | 2/2015 | Schmidt et al. |
| 2015/0051616 A1 | 2/2015 | Haasl et al. |
| 2015/0051682 A1 | 2/2015 | Schmidt et al. |
| 2015/0094668 A1 | 4/2015 | Wood et al. |
| 2015/0094735 A1* | 4/2015 | Ward ............... A61N 1/37205 606/129 |
| 2015/0273207 A1 | 10/2015 | Tran et al. |
| 2015/0273212 A1* | 10/2015 | Berthiaume ........ A61N 1/0587 600/424 |
| 2015/0283376 A1 | 10/2015 | Ollivier et al. |
| 2015/0306378 A1 | 10/2015 | Schmidt et al. |
| 2015/0306381 A1 | 10/2015 | Schmidt et al. |
| 2015/0335884 A1 | 11/2015 | Khairkhahan et al. |
| 2015/0352351 A1 | 12/2015 | Muessig et al. |
| 2016/0000563 A1 | 1/2016 | Asleson et al. |
| 2016/0007924 A1 | 1/2016 | Eigler et al. |
| 2016/0015287 A1 | 1/2016 | Anderson et al. |
| 2016/0015322 A1 | 1/2016 | Anderson et al. |
| 2016/0059003 A1 | 3/2016 | Eggen et al. |
| 2016/0067446 A1 | 3/2016 | Klenk et al. |
| 2016/0067447 A1 | 3/2016 | Paspa et al. |
| 2016/0067503 A1 | 3/2016 | Berthiaume et al. |
| 2016/0082270 A1 | 3/2016 | Mothilal et al. |
| 2016/0096001 A1 | 4/2016 | Eidenschink et al. |
| 2016/0114157 A1 | 4/2016 | Haasl et al. |
| 2016/0158560 A1 | 6/2016 | Moore et al. |
| 2016/0206872 A1 | 7/2016 | Wood et al. |
| 2016/0213919 A1 | 7/2016 | Suwito et al. |
| 2016/0220829 A1* | 8/2016 | Wood ............... A61N 1/3756 |
| 2016/0228715 A9 | 8/2016 | Bonner et al. |
| 2016/0235971 A1 | 8/2016 | Wood et al. |
| 2016/0243350 A9 | 8/2016 | Grubac et al. |
| 2016/0243355 A1 | 8/2016 | Wood |
| 2016/0263372 A1 | 9/2016 | Wood et al. |
| 2016/0271388 A1 | 9/2016 | Ollivier et al. |
| 2016/0279423 A1 | 9/2016 | Kelly et al. |
| 2016/0296761 A1 | 10/2016 | Doan et al. |
| 2016/0310703 A1 | 10/2016 | Drake et al. |
| 2016/0310723 A1 | 10/2016 | Eggen et al. |
| 2016/0310726 A1 | 10/2016 | Demmer et al. |
| 2016/0310747 A1 | 10/2016 | Grubac et al. |
| 2016/0325104 A1 | 11/2016 | Anderson et al. |
| 2016/0361536 A1 | 12/2016 | Grubac et al. |
| 2017/0028190 A1 | 2/2017 | O'Carroll et al. |
| 2017/0028194 A1 | 2/2017 | Bonner et al. |
| 2017/0043158 A1 | 2/2017 | Kelly et al. |
| 2017/0065369 A1 | 3/2017 | Bornzin et al. |
| 2017/0072191 A1 | 3/2017 | Ma et al. |
| 2017/0095662 A1 | 4/2017 | McDonnell et al. |
| 2017/0100582 A1 | 4/2017 | McEvoy et al. |
| 2017/0106185 A1 | 4/2017 | Orts et al. |
| 2017/0113035 A1 | 4/2017 | Bonner et al. |
| 2017/0119999 A1 | 5/2017 | Kelly |
| 2017/0136231 A1 | 5/2017 | Kelly et al. |
| 2017/0143955 A1 | 5/2017 | Soltis et al. |
| 2017/0143980 A1 | 5/2017 | Soltis et al. |
| 2017/0151429 A1 | 6/2017 | Regnier |
| 2017/0165479 A1 | 6/2017 | Rys et al. |
| 2017/0189681 A1 | 7/2017 | Anderson |
| 2017/0209688 A1 | 7/2017 | Drake et al. |
| 2017/0209689 A1 | 7/2017 | Chen et al. |
| 2017/0209690 A1 | 7/2017 | Drake et al. |
| 2017/0216575 A1 | 8/2017 | Asleson et al. |
| 2017/0224997 A1 | 8/2017 | Shuros et al. |
| 2017/0274202 A1 | 9/2017 | Grubac et al. |
| 2017/0304624 A1 | 10/2017 | Friedman et al. |
| 2017/0312479 A1 | 11/2017 | Keaveney et al. |
| 2017/0312496 A1 | 11/2017 | Wood et al. |
| 2017/0319847 A1 | 11/2017 | Ho et al. |
| 2017/0326369 A1 | 11/2017 | Koop et al. |
| 2017/0326372 A1 | 11/2017 | Koop et al. |
| 2017/0326373 A1 | 11/2017 | Delanely, Jr. et al. |
| 2017/0340316 A1 | 11/2017 | Wood et al. |
| 2017/0340877 A1 | 11/2017 | Ollivier |
| 2017/0368338 A1 | 12/2017 | Madden et al. |

FOREIGN PATENT DOCUMENTS

| | | |
|---|---|---|
| EP | 2651502 B1 | 11/2016 |
| EP | 2771064 B1 | 1/2017 |
| EP | 2780077 B1 | 1/2017 |

* cited by examiner

DELIVERY DEVICES AND METHODS FOR LEADLESS CARDIAC DEVICES

CROSS REFERENCE TO RELATED APPLICATIONS

The present application claims the benefit of and priority to U.S. Provisional Patent Application Ser. No. 62/439,261, filed Dec. 27, 2016, the disclosure of which is incorporated herein by reference.

TECHNICAL FIELD

The present disclosure pertains to medical devices, and methods for manufacturing and/or using medical devices. More particularly, the present disclosure pertains to leadless cardiac devices and methods, such as leadless pacing devices and methods, and delivery devices and methods for such leadless devices.

BACKGROUND

A wide variety of medical devices have been developed for medical use, for example, cardiac use. Some of these devices include catheters, leads, pacemakers, and the like, and delivery devices and/or systems used for delivering such devices. These devices are manufactured by any one of a variety of different manufacturing methods and may be used according to any one of a variety of methods. Of the known medical devices, delivery systems, and methods, each has certain advantages and disadvantages. There is an ongoing need to provide alternative medical devices and delivery devices as well as alternative methods for manufacturing and using medical devices and delivery devices.

BRIEF SUMMARY

This disclosure provides design, material, manufacturing method, and use alternatives for medical devices, including delivery devices.

In a first example, a delivery device for delivering an implantable leadless pacing device may comprise an outer tubular member including a lumen extending from a proximal end to a distal end thereof, an intermediate tubular member including a lumen extending from a proximal end to a distal end thereof, the intermediate tubular member slidably disposed within the lumen of the outer tubular member and the intermediate tubular member including a distal holding section defining a cavity therein for receiving an implantable leadless pacing device, and an inner tubular member including a lumen extending from a proximal end to a distal end thereof, the inner tubular member slidably disposed within the lumen of the intermediate tubular member At least a portion of the lumen of the inner tubular member may be bifurcated to form a first lumen and a second lumen, the first lumen configured to receive a first portion of a tether and the second lumen configured to receive a second portion of the tether.

Alternatively or additionally to any of the examples above, in another example, the first and second lumen may be separated by a wall extending across the lumen of the inner tubular member.

Alternatively or additionally to any of the examples above, in another example, the delivery device may further comprise a funnel coupled to the distal end of the inner tubular member, the lumen of the inner tubular member extending through the funnel.

Alternatively or additionally to any of the examples above, in another example, the first and second lumens may extend along less than an entire length of the lumen of the inner tubular member and may be positioned within the funnel.

Alternatively or additionally to any of the examples above, in another example, the first and second lumens may extend along less than an entire length of the lumen of the inner tubular member and may be positioned within a distal end region of the inner tubular member.

Alternatively or additionally to any of the examples above, in another example, the first and second lumens may extend along less than an entire length of the lumen of the inner tubular member and may be positioned within an intermediate end region of the inner tubular member between the proximal end and the distal end thereof.

Alternatively or additionally to any of the examples above, in another example, the first and second lumens may extend along less than an entire length of the lumen of the inner tubular member and may be positioned within a proximal end region of the inner tubular member.

Alternatively or additionally to any of the examples above, in another example, the first and second lumens may extend from the proximal end of the inner tubular member to the distal end of the inner tubular member.

Alternatively or additionally to any of the examples above, in another example, the first and second lumens may extend from the proximal end of the inner tubular member and into the funnel.

In another example a method for assembling a tether with an implantable leadless pacing device and a delivery device may comprise advancing a free end of a tether through a first lumen of a bifurcated lumen of a tubular member of a delivery device for delivering an implantable leadless pacing device, advancing the free end of the tether through an opening of the implantable leadless pacing device, and advancing the free end of the tether through a second lumen of the bifurcated lumen of the tubular member of the delivery device.

Alternatively or additionally to any of the examples above, in another example, a vacuum may be used to pull the free end of the tether from a distal end of the delivery device to a proximal end of the delivery device.

Alternatively or additionally to any of the examples above, in another example, a stylet may be used to guide the free end of the tether during the steps of advancing the free end of the tether through the first lumen of the bifurcated lumen, the opening of the implantable leadless pacing device, and the second lumen of the bifurcated lumen.

Alternatively or additionally to any of the examples above, in another example, the bifurcated lumen may be positioned adjacent to a distal end of the tubular member.

Alternatively or additionally to any of the examples above, in another example, the bifurcated lumen may be positioned adjacent to a proximal end of the tubular member.

Alternatively or additionally to any of the examples above, in another example, the bifurcated lumen may extend from a proximal end to a distal end of the tubular member.

In another example a delivery device for delivering an implantable leadless pacing device may comprise an outer tubular member including a lumen extending from a proximal end to a distal end thereof, an intermediate tubular member including a lumen extending from a proximal end to a distal end thereof, the intermediate tubular member slidably disposed within the lumen of the outer tubular member and the intermediate tubular member including a distal holding section defining a cavity therein for receiving an implantable leadless pacing device, and an inner tubular member including a lumen extending from a proximal end to a distal end thereof, the inner tubular member slidably disposed within the lumen of the intermediate tubular member. At least a portion of the lumen of the inner tubular member may be bifurcated to form a first lumen and a second lumen, the first lumen configured to receive a first portion of a tether and the second lumen configured to receive a second portion of the tether.

Alternatively or additionally to any of the examples above, in another example, the first and second lumen may be separated by a wall extending across the lumen of the inner tubular member.

Alternatively or additionally to any of the examples above, in another example, the delivery device may further comprise a funnel coupled to the distal end of the inner tubular member, the lumen of the inner tubular member extending through the funnel.

Alternatively or additionally to any of the examples above, in another example, the first and second lumens may extend along less than an entire length of the lumen of the inner tubular member and may be positioned within the funnel.

Alternatively or additionally to any of the examples above, in another example, the first and second lumens may extend along less than an entire length of the lumen of the inner tubular member and may be positioned within a distal end region of the inner tubular member.

Alternatively or additionally to any of the examples above, in another example, the first and second lumens may extend along less than an entire length of the lumen of the inner tubular member and may be positioned within an intermediate end region of the inner tubular member between the proximal end and the distal end thereof.

Alternatively or additionally to any of the examples above, in another example, the first and second lumens may extend along less than an entire length of the lumen of the inner tubular member and may be positioned within a proximal end region of the inner tubular member.

Alternatively or additionally to any of the examples above, in another example, the first and second lumens may extend from the proximal end of the inner tubular member to the distal end of the inner tubular member.

Alternatively or additionally to any of the examples above, in another example, the first and second lumens may extend from the proximal end of the inner tubular member and into the funnel.

In another example a delivery device for delivering an implantable leadless pacing device may comprise an outer tubular member including a lumen extending from a proximal end to a distal end thereof, an intermediate tubular member including a lumen extending from a proximal end to a distal end thereof, the intermediate tubular member slidably disposed within the lumen of the outer tubular member and the intermediate tubular member including a distal holding section defining a cavity therein for receiving an implantable leadless pacing device, an inner tubular member including a lumen extending from a proximal end to a distal end thereof, the inner tubular member slidably disposed within the lumen of the intermediate tubular member, a funnel coupled to the distal end of the inner tubular member, the lumen of the inner tubular member extending through the funnel, and a handle assembly coupled to the proximal end of the outer tubular member, the proximal end of the intermediate tubular member, and the proximal end of the inner tubular member. A wall may extend across a width of the lumen of the inner tubular member along at least a portion of a length of the lumen to bifurcate the lumen into a first lumen and a second lumen.

Alternatively or additionally to any of the examples above, in another example, the wall may extend along less than an entire length of the lumen of the inner tubular member and may be positioned within the funnel.

Alternatively or additionally to any of the examples above, in another example, the first and second lumens may extend along less than an entire length of the lumen of the inner tubular member and may be positioned within a distal end region of the inner tubular member.

Alternatively or additionally to any of the examples above, in another example, the first and second lumens may extend along less than an entire length of the lumen of the inner tubular member and may be positioned within a proximal end region of the inner tubular member.

Alternatively or additionally to any of the examples above, in another example, the first and second lumens may extend from the proximal end of the inner tubular member to the distal end of the inner tubular member.

In another example a method for assembling a tether with an implantable leadless pacing device and a delivery device may comprise advancing a free end of a tether through a first lumen of a bifurcated lumen of a tubular member of a delivery device for delivering an implantable leadless pacing device, advancing the free end of the tether through an opening of the implantable leadless pacing device, and advancing the free end of the tether through a second lumen of the bifurcated lumen of the tubular member of the delivery device.

Alternatively or additionally to any of the examples above, in another example, a vacuum may be used to pull the free end of the tether from a distal end of the delivery device to a proximal end of the delivery device.

Alternatively or additionally to any of the examples above, in another example, a stylet may be used to guide the free end of the tether during the steps of advancing the free end of the tether through the first lumen of the bifurcated lumen, the opening of the implantable leadless pacing device, and the second lumen of the bifurcated lumen.

Alternatively or additionally to any of the examples above, in another example, the bifurcated lumen may be positioned adjacent a distal end of the tubular member.

Alternatively or additionally to any of the examples above, in another example, the bifurcated lumen may be positioned adjacent to a proximal end of the tubular member.

Alternatively or additionally to any of the examples above, in another example, the bifurcated lumen may extend from a proximal end to a distal end of the tubular member.

The above summary of some embodiments is not intended to describe each disclosed embodiment or every implementation of the present disclosure. The Figures, and Detailed Description, which follow, more particularly exemplify some of these embodiments.

BRIEF DESCRIPTION OF THE DRAWINGS

The disclosure may be more completely understood in consideration of the following detailed description in connection with the accompanying drawings, in which.

Figure 1:
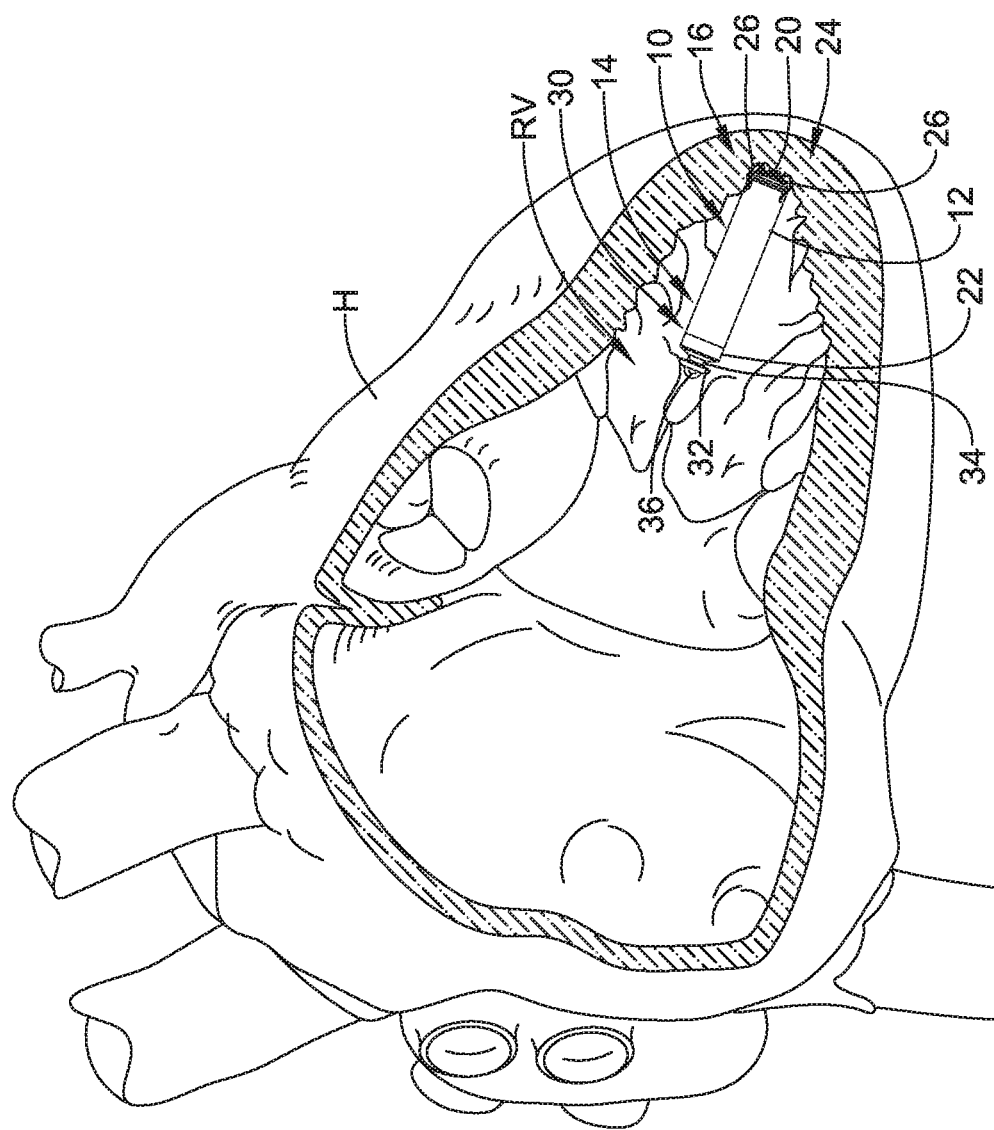
FIG. 1 is a plan view of an example leadless pacing device implanted within a heart.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar structures in different drawings are numbered the same. The drawings, which are not necessarily to scale, depict illustrative embodiments and are not intended to limit the scope of the disclosure.

Cardiac pacemakers provide electrical stimulation to heart tissue to cause the heart to contract and thus pump blood through the vascular system. Conventional pacemakers typically include an electrical lead that extends from a pulse generator implanted subcutaneously or sub-muscularly to an electrode positioned adjacent the inside or outside wall of the cardiac chamber. As an alternative to conventional pacemakers, self-contained or leadless cardiac pacemakers have been proposed. Leadless cardiac pacemakers are small capsules typically fixed to an intracardiac implant site in a cardiac chamber. The small capsule typically includes bipolar pacing/sensing electrodes, a power source (e.g., a battery), and associated electrical circuitry for controlling the pacing/sensing electrodes, and thus provide electrical stimulation to heart tissue and/or sense a physiological condition. The capsule may be delivered to the heart using a delivery device which may be advanced through a femoral vein, into the inferior vena cava, into the right atrium, through the tricuspid valve, and into the right ventricle. Accordingly, it may be desirable to provide delivery devices which facilitate advancement through the vasculature.

Figure 2:
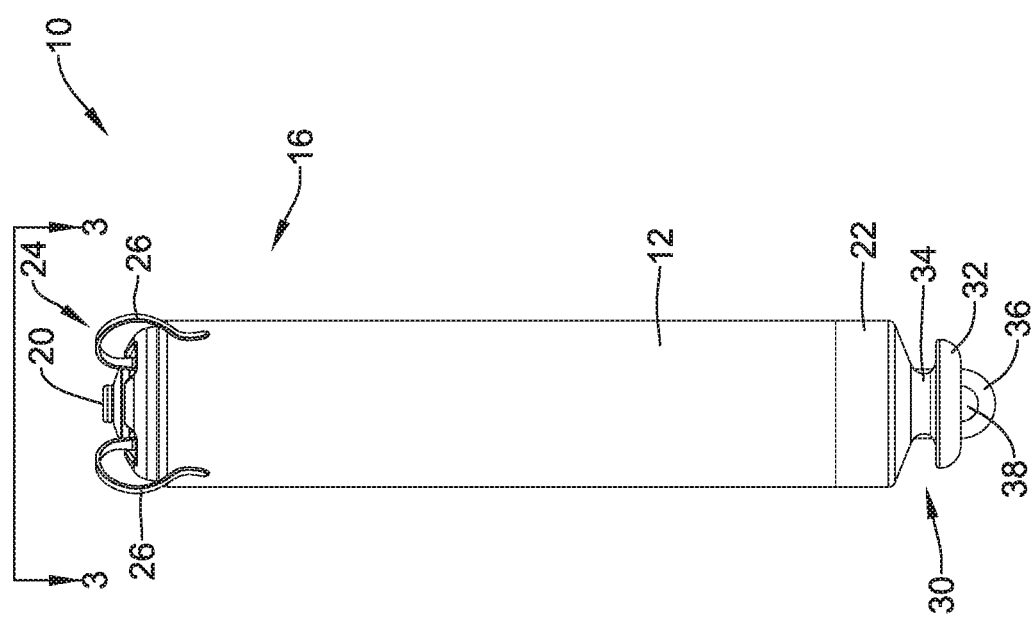
FIG. 2 is a side view of an example implantable leadless cardiac pacing device.
Figure 3:
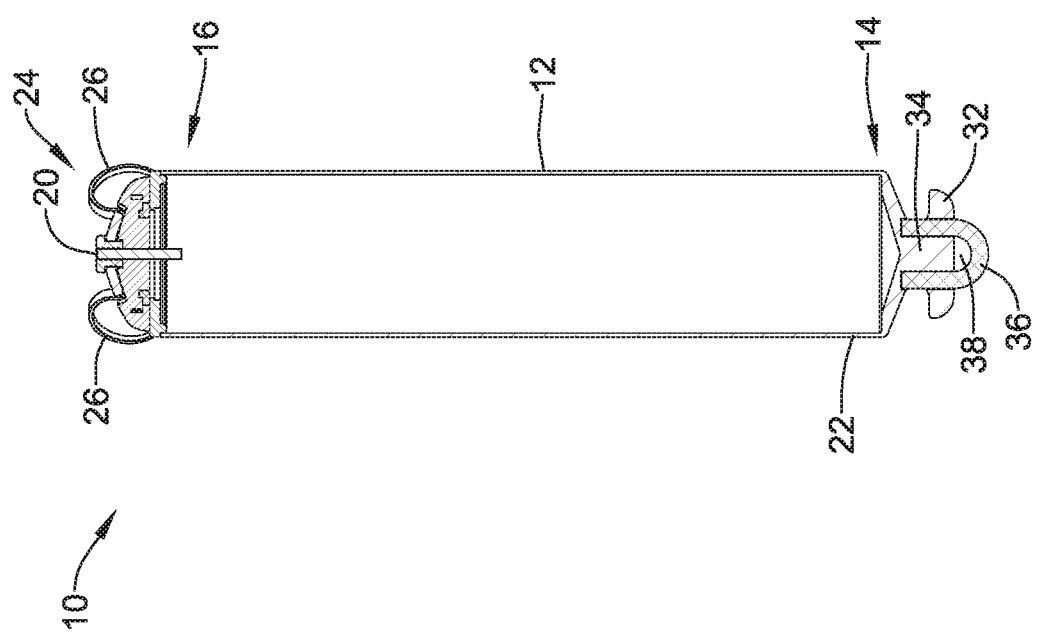
FIG. 3 is a cross-sectional view of the implantable leadless cardiac pacing device of FIG. 2.

FIG. 1 illustrates an example implantable leadless cardiac pacing device 10 (e.g., a leadless pacemaker) implanted in a chamber of a heart H, such as the right ventricle RV. A side view of the illustrative implantable device 10 is shown in FIG. 2 and a cross-sectional view of the illustrative implantable device 10, taken at line 3-3 in FIG. 2, is illustrated in FIG. 3. The implantable device 10 may include a shell or housing 12 having a proximal end 14 and a distal end 16. The implantable device 10 may include a first electrode 20 positioned adjacent to the distal end 16 of the housing 12 and a second electrode 22 positioned adjacent to the proximal end 14 of the housing 12. For example, housing 12 may include a conductive material and may be insulated along a portion of its length. A section along the proximal end 14 may be free of insulation so as to define the second electrode 22. The electrodes 20, 22 may be sensing and/or pacing electrodes to provide electro-therapy and/or sensing capabilities. The first electrode 20 may be capable of being positioned against or may otherwise contact the cardiac tissue of the heart H while the second electrode 22 may be spaced away from the first electrode 20, and thus spaced away from the cardiac tissue.

The implantable device 10 may include a pulse generator (e.g., electrical circuitry) and a power source (e.g., a battery) within the housing 12 to provide electrical signals to the electrodes 20, 22 and thus control the pacing/sensing electrodes 20, 22. Electrical communication between the pulse generator and the electrodes 20, 22 may provide electrical stimulation to heart tissue and/or sense a physiological condition.

The implantable device 10 may include a fixation mechanism 24 proximate the distal end 16 of the housing 12 configured to attach the implantable device 10 to a tissue wall of the heart H, or otherwise anchor the implantable device 10 to the anatomy of the patient. As shown in FIG. 1, in some instances, the fixation mechanism 24 may include one or more, or a plurality of hooks or tines 26 anchored into the cardiac tissue of the heart H to attach the implantable device 10 to a tissue wall. In other instances, the fixation mechanism 24 may include one or more, or a plurality of passive tines, configured to entangle with trabeculae within the chamber of the heart H and/or a helical fixation anchor configured to be screwed into a tissue wall to anchor the implantable device 10 to the heart H.

The implantable device 10 may include a docking member 30 proximate the proximal end 14 of the housing 12 configured to facilitate delivery and/or retrieval of the implantable device 10. For example, the docking member 30 may extend from the proximal end 14 of the housing 12 along a longitudinal axis of the housing 12. The docking member 30 may include a head portion 32 and a neck portion 34 extending between the housing 12 and the head portion 32. The head portion 32 may be an enlarged portion relative to the neck portion 34. For example, the head portion 32 may have a radial dimension from the longitudinal axis of the implantable device 10 which is greater than a radial dimension of the neck portion 34 from the longitudinal axis of the implantable device 10. The docking member 30 may further include a tether retention structure 36 extending from the head portion 32. The tether retention structure 36 may define an opening 38 configured to receive a tether or other anchoring mechanism therethrough. While the retention structure 36 is shown as having a generally "U-shaped" configuration, the retention structure 36 may take any shape which provides an enclosed perimeter surrounding the opening 38 such that a tether may be securably and releasably passed (e.g., looped) through the opening 38. The retention structure 36 may extend through the head portion 32, along the neck portion 34, and to or into the proximal end 14 of the housing 12, as is shown more clearly in FIG. 3. The docking member 30 may be configured to facilitate delivery of the implantable device 10 to the intracardiac site and/or retrieval of the implantable device 10 from the intracardiac site. Other docking members 30 are contemplated.

One aspect of the current disclosure relates to the delivery device and/or system used, for example, to deliver device 10 to a suitable location within the anatomy (e.g., the heart). As may be appreciated, the delivery device may need to be navigated through relatively tortuous anatomy to deliver the device 10 to a suitable location. For instance, in some embodiments, the delivery device may be advanced through the vasculature to a target region. In some example cases the device may be advanced through a femoral vein, into the inferior vena cava, into the right atrium, through the tricuspid valve, and into the right ventricle. The target region for the delivery of the device 10 may be a portion of the right ventricle, for example, a portion of the right ventricle near the apex of the heart. The target region may also include other regions of the heart (e.g., right atrium, left atrium, or left ventricle), blood vessels, or other suitable targets. It may be desirable to provide the delivery system with certain features that may allow for easier or better control for navigation or delivery purposes.

Maintaining control of the device 10 during delivery thereof is critical for the safety of the patient. For example, maintaining control may help ensure the device 10 does not dislodge from the delivery device and embolize the patient. A tether or other retaining feature may be used to releasably secure the device 10 to the delivery device. The tether may form a loop that extends distally through a lumen of the delivery device to the device 10 and proximally back to a proximal end of the delivery device. Cutting one strand of the loop and proximally pulling the tether to release it from the device 10 may enable the final delivery of the device 10. However, during assembly of the device 10 with the delivery device, implant preparation, and/or during implant it may be important to minimize tether twisting and/or tangling to reduce the potential for increased removal resistance of the tether. It may be desirable to provide the delivery system with certain features that reduce and/or minimize twisting and/or tangling of the tether.

Figure 4:
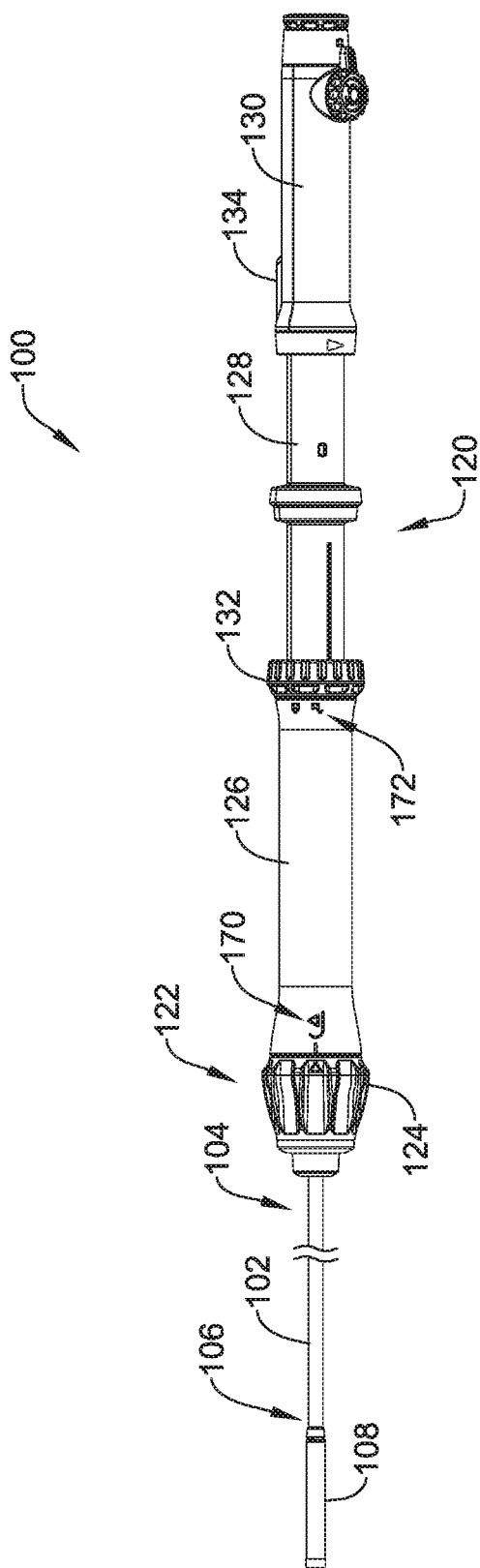
FIG. 4 is a plan view of an example delivery device for an implantable leadless cardiac pacing device.

FIG. 4 is a plan view of an illustrative delivery device 100, such as a catheter, that may be used to deliver the implantable device 10. The delivery device 100 may include an outer tubular member 102 having a proximal section 104 and a distal section 106. An intermediate tubular member 110 may be longitudinally slidably disposed within a lumen 150 of the outer tubular member 102 (see e.g., FIG. 5). An inner tubular member 116 may be longitudinally slidably disposed within a lumen 152 of the intermediate tubular member 110 (see e.g., FIG. 5). A distal holding section 108 may be attached to a distal end portion 114 of the intermediate tubular member 110. The delivery device 100 may also include a handle assembly 120 positioned adjacent to the proximal section 104 of the outer tubular member 102. In some embodiments, the outer tubular member 102 may include at least a section thereof that has an outer diameter D2 that is less than the outer diameter D1 of at least a portion of the holding section 108 (see e.g., FIG. 5).

Figure 5:
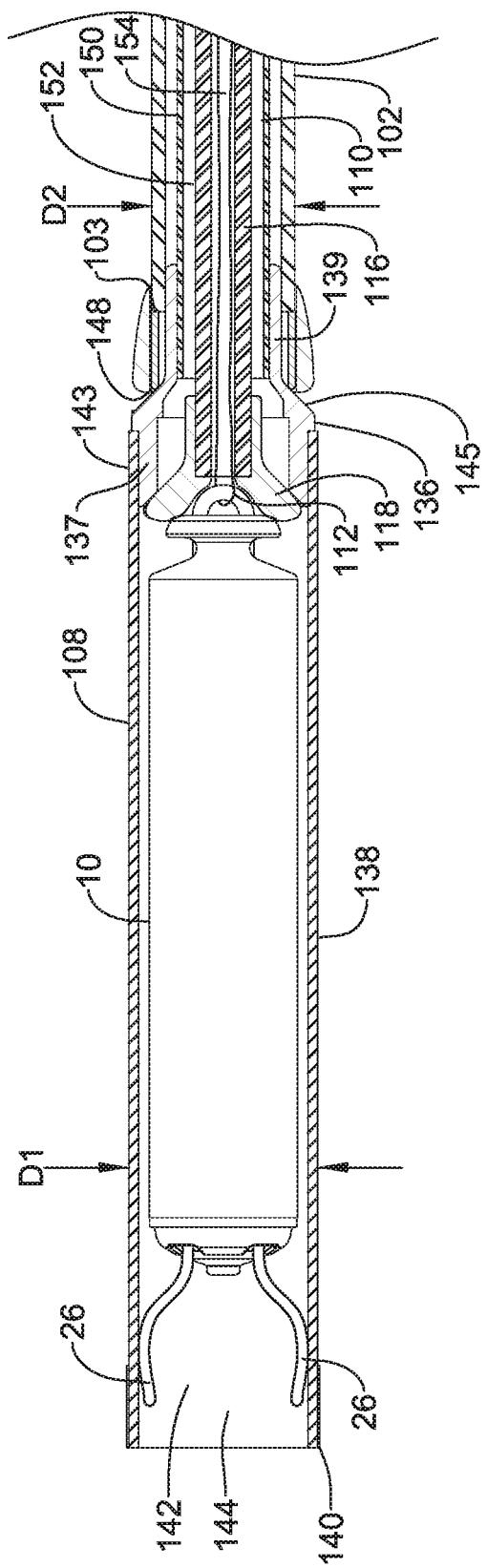
FIG. 5 is a partial cross-sectional side view of the distal portion of the delivery device of FIG. 4.

The handle assembly 120 may include a first or distal hub portion 126 attached to, such as fixedly attached to, the proximal end section 104 of the outer tubular member 102, a second or intermediate hub portion 128 attached to, such as fixedly attached to, a proximal end section of the intermediate tubular member 110, and a third or proximal hub portion 130 attached to, such as fixedly attached to, a proximal end section of the inner tubular member 116 (see e.g., FIG. 5). The first hub portion 126, second hub portion 128, and third hub portion 130 may be positioned in a generally telescoping arrangement and longitudinally slidable relative to each other. Each of the first hub portion 126, the second hub portion 128, and the third hub portion 130 may be longitudinally slidable and rotatable relative to each other such that the outer tubular member 102, intermediate tubular member 110, and inner tubular member 116 may be individually actuated. In some instances, it may be desirable to move the outer tubular member 102, intermediate tubular member 110 and inner tubular member 116 simultaneously. The handle assembly 120 may include a multi-stage deployment mechanism or a first locking mechanism 134 to releasably couple the second hub portion 128 to the third hub portion 130 to prevent relative longitudinal movement therebetween, and thus prevent relative longitudinal movement between the intermediate tubular member 110 and the inner tubular member 116. The handle assembly 120 may also include a second locking mechanism 132 disposed on a proximal end 172 of the first hub portion 126 to releasably couple the first hub portion 126 to the second hub portion 128 to prevent relative longitudinal movement therebetween, and thus prevent relative longitudinal movement between the outer tubular member 102 and the intermediate tubular member 110.

The distal holding section 108 may be configured to receive the implantable device 10 therein. For example, referring to FIG. 5, which illustrates a cross-sectional view of a distal portion of delivery device 100, the holding section 108 may define a cavity 142 for slidably receiving the implantable device 10, and may include a distal opening 144 for slidable insertion and/or extraction of the implantable device 10 into and/or out of the cavity 142.

The distal holding section 108 may include a body portion 138 and a distal tip portion 140 that may be, for example, configured to be atraumatic to anatomy, such as a bumper tip. For example, as the catheter is navigated through the anatomy, the distal tip 140 may come into contact with anatomy. Additionally, when the catheter is used to deliver the device, the tip 140 of the delivery device 100 will likely come into contact with tissue adjacent the target site (e.g., cardiac tissue of the heart). A hard distal tip formed of the material of the outer tubular member 102 and/or intermediate tubular member 110 may injure a vessel wall or cardiac tissue. As such, it may be desirable to provide the delivery device 100 with a softer distal tip 140 that can be introduced into the anatomy and come into contact with anatomy adjacent the target cite without causing unnecessary trauma.

For example, the distal tip 140 may be made of a material that is softer than the body portion 138 of the distal holding section. In some cases, the distal tip 140 may include a material that has a durometer that is less than the durometer of the material of the body portion 138. In some particular embodiments, the durometer of the material used in the distal tip 140 may be in the range of about 5 D to about 70 D, or for example, in the range of about 25 D to about 65 D. Additionally, the distal tip 140 may include a shape or structure that may make it less traumatic to tissue. For example, the distal tip 140 may have a distal surface, such as a tissue contacting surface, that is that is rounded or includes a curvature configured to be more atraumatic to tissue.

In some embodiments, all or a portion of the distal holding section 108 may include an inner surface that may be configured to resist getting caught on the fixation mechanism 24, such as the one or more, or a plurality of hooks or tines 26 on the device 10. For example, the distal holding section 108 may include an inner layer or coating of harder or more lubricious material that resists force applied by the fixation mechanism 24 onto the inner surface of the distal holding section 108. For example, the distal holding section 108 may include a multi-layered structure, and an inner layer may be made of a material that is harder than an outer layer.

The inner tubular member 116 may be disposed (e.g., slidably disposed) within a lumen 152 of the intermediate tubular member 110. The inner tubular member 116 may be engaged by a user near or at the third hub portion 130, and extend through a lumen 152 of the intermediate tubular member 110 and into the distal holding section 108. A distal portion 118 of the inner tubular member 116 may be capable of engaging the device 10, and the inner tubular member 116 may be used to "push" the device 10 out from distal holding section 108 so as to deploy and anchor device 10 within a target region (e.g., a region of the heart such as the right ventricle). The inner tubular member 116 may have a lumen 154 extending from the proximal end 117 to a distal portion 118 thereof. A tether 112 or other retaining feature may be used to releasably secure the device 10 to the delivery device 100. In some instances, the tether 112 may be a single or unitary length of material that may extend from a proximal end 117 of the lumen 154, out through the distal portion 118, through the opening 38 of the device 10 and return to the proximal end 117 of the inner tubular member 116 through the lumen 154 such that both ends of the tether 112 are positioned adjacent to the third hub portion 130. In some instances, the ends of the tether 112 may be secured within a locking feature in the third hub portion 130.

In order to more specifically place or steer the delivery device 100 to a position adjacent to the intended target, the delivery device 100 may be configured to be deflectable or articulable or steerable. Referring to FIG. 4, for example, the outer tubular member 102 and/or intermediate tubular member 110 may include one or more articulation or deflection mechanism(s) that may allow for the delivery device 100, or portions thereof, to be deflected, articulated, steered and/or controlled in a desired manner. For example, the outer tubular member 102 may include at least a portion thereof that can be selectively bent and/or deflected in a desired or predetermined direction. This may, for example, allow a user to orient the delivery device 100 such that the holding section 108 is in a desirable position or orientation for navigation or delivery of the device 10 to a target location.

The outer tubular member 102 may be deflected, for example, along a deflection region.

A wide variety of deflection mechanisms may be used. In some example embodiments, deflection may be effected by one or more actuation members, such as pull wire(s) extending between a distal portion of the outer tubular member 102 and an actuation mechanism 122 near the proximal end of the outer tubular member 102. As such, the one or more pull wires may extend both proximally and distally of the desired deflection or bending region or point. This allows a user to actuate (e.g., "pull") one or more of the pull wires to apply a compression and/or deflection force to at least a portion of the outer tubular member 102 and thereby deflect or bend the outer tubular member 102 in a desired manner. In addition, in some cases the one or more wires may be stiff enough so that they can also be used to provide a pushing and/or tensioning force on the outer tubular member 102, for example, to "push" or "straighten" the shaft into a desired position or orientation.

In some embodiments, the actuation member takes the form of a continuous wire that is looped through or otherwise coupled to a distal end region of the outer tubular member 102 so as to define a pair of wire sections. Other embodiments are contemplated, however, including embodiments where the actuation member includes one or a plurality of individual wires that are attached, for example, to a metal or metal alloy ring adjacent the distal end region of the outer tubular member 102.

The actuation mechanism 122 may include a mechanism that may allow for applying tension (i.e. pulling force), or compression (i.e. pushing force), or both, on the actuation member(s). In some embodiments, the actuation mechanism 122 may include an external rotatable member 124 connected to a distal region 170 of the distal hub portion 126 and rotatable about the longitudinal axis of the handle assembly 120. The rotatable member 124 may threadingly engage an internal member that is attached to the proximal end of the actuation member(s) or pull wires. When the external rotatable member 124 is rotated in a first rotational direction, the internal member translates in a first longitudinal direction, thereby applying tension to the pull wire(s), which applies compression force to the shaft, so as to deflect the outer tubular member 102 from an initial position to a deflected position. When the external rotatable member 124 is rotated in a second rotational direction, the internal member translates in a second longitudinal direction, thereby reducing and/or releasing the tension on the pull wire(s), and allowing the outer tubular member 102 to relax back toward the initial position. Additionally, in some cases, as mentioned above, where the one or more wires may be stiff enough, rotation of the rotatable member 124 in the second rotational direction such that the internal member translates in a second longitudinal direction may apply compression to the wire(s), such that the wire(s) may apply tension to the outer tubular member 102 and "push" the outer tubular member 102 back toward an initial position, and possibly into additional positions beyond the initial position.

The one or more articulation and/or deflection mechanism(s) may also entail the outer tubular member 102 including structure and/or material that may provide for the desired degree and/or location of the deflection when the compressive or tensile forces are applied. For example, the outer tubular member 102 may include one or more sections that include structure and/or material configured to allow the shaft to bend and/or deflect in a certain way when a certain predetermined compressive and/or tensile force is applied. For example, the shaft may include one or more sections that are more flexible than other sections, thereby defining a bending or articulating region or location. Some such regions may include a number of varying or changing flexibility characteristics that may define certain bending shapes when predetermined forces are applied. Such characteristics may be achieved through the selection of materials or structure for different sections of the outer tubular member 102.

In other embodiments, other articulation and/or deflection mechanism(s) are contemplated. For example, all or a portion of the delivery device 100, such as the outer tubular member 102, may be made of a shape memory material, such as a shape memory polymer and/or a shape memory metal. Such materials, when stimulated by an actuation mechanism, such as a change in temperature or the application of an electrical current, may change or move from a first shape to a second shape. As such, these material and mechanism may be used to deflect or bend the outer tubular member 102 in a desired manner. Other suitable deflection mechanism(s) that are able to deflect the delivery device 100 may also be used. Such alternative mechanisms may be applied to all other embodiments shown and/or discussed herein, and others, as appropriate.

Furthermore, the outer tubular member 102 may include one or more predefined or fixed curved portion(s) along the length thereof. In some cases, such curved sections may be configured to fit with particular anatomies or be configured for better navigation or delivery of the device 10. Additionally, or alternatively, some such curved sections may be configured to allow the outer tubular member 102 to be predisposed to be bent and/or deflected in a certain direction or configuration when compression and/or tension forces are applied thereto. It is contemplated that the outer tubular member 102 may be a laser cut metallic tubing, a braid reinforced polymeric tubing, or other flexible tubular structure as desired.

Returning again to FIG. 5, the distal holding section 108 may be affixed to a distal end portion 114 of the intermediate tubular member 110. The distal holding section 108 may include a hub portion 136 and a tubular body portion 138. In some instances, the hub portion 136 may be formed from a metal or metal alloy while the body portion 138 may be formed from a polymeric material, although this is not required. In some instances, a proximal region 143 of the body portion 138 may be heat bonded to a distal end portion 137 of the hub portion 136, or otherwise affixed. The hub portion 136 may include a tapered intermediate region 145 disposed between a proximal end portion 139 and the distal end portion 137.

In some embodiments, the outer tubular member 102 may include a metal ring or tip adjacent the distal end 103 thereof for attaching one or more pull wires thereto. It is contemplated that the outer tubular member 102 may further include a lubricious liner, such as, but not limited to a polytetrafluoroethylene (PTFE) liner. The proximal end portion 139 of the hub portion 136 may extend proximally into the lumen 150 of the outer tubular member 102. In some instances, an outer surface of the proximal end portion 139 may form an interference fit with an inner surface of the outer tubular member 102. It is contemplated that the outer surface of the proximal end portion 139 and the inner surface of the outer tubular member 102 may be coupled in a tapered engagement. For example, the distal end 103 of the outer tubular member 102 may flare radially outwards in the distal direction and/or the proximal end portion 139 may taper radially inward in the proximal direction. The two angled surface may engage as the proximal end portion 139 is proximally retracted within the outer tubular member 102. Other coupling arrangements may be used as desired.

It is contemplated that as the outer tubular member 102 is bent to navigate the implantable device 10 to the desired location, the proximal end portion 139 may advance distally and disengage from the inner surface of the outer tubular member 102 creating a kink point or weakened region adjacent to the bonding region 146. Proximally retracting the intermediate tubular member 110 to bring the intermediate region 145 into contact with the outer tubular member 102 at contact point 148 and/or bringing the proximal end portion 139 into the outer tubular member 102 and fixing the intermediate tubular member 110 in this configuration may help prevent migration of the distal holding section 108 during navigation of the delivery device 100 to the desired location. Such a configuration may also place the intermediate tubular member 110 in tension while the distal holding section 108 applies a compression force on the outer tubular member 102, as will be discussed in more detail below. As discussed above, a locking mechanism 132 in the handle assembly 120 may be utilized to releasably maintain the outer tubular member 102 and the intermediate tubular member 110 in a desired orientation.

Figure 6A:
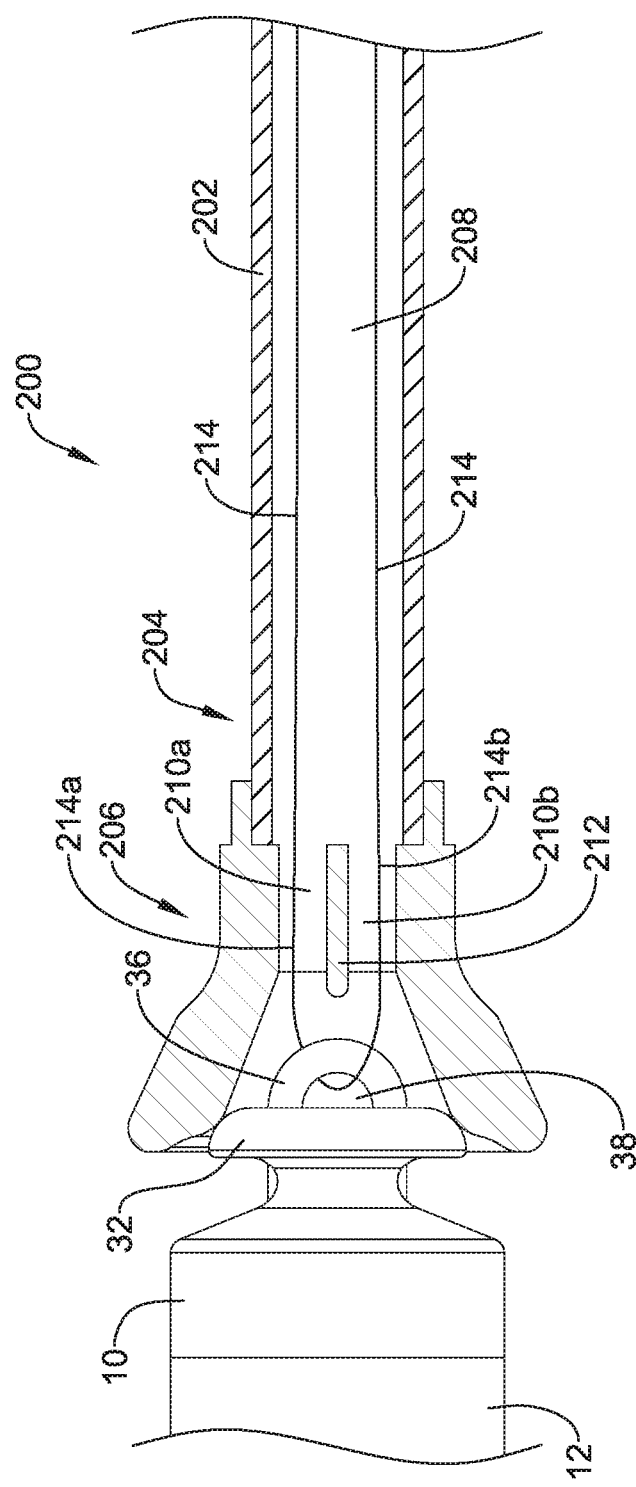
FIG. 6A is a partial cross-sectional side view of the distal portion of an alternative delivery device.

FIG. 6A is a partial cross-section of a distal portion of an alternative delivery device 200. The delivery device 200 may be similar in form and function to the delivery device 100 described above. However, for clarity some portions of the delivery device 200 are not illustrated including, but not limited to the outer tubular member, the intermediate tubular member, the distal holding section, and the handle assembly. It should be understood that while not shown these components may be present in the delivery device 200 and substantially the same as those described with respect to FIGS. 4 and 5.

The delivery device 200 may include an inner tubular member 202 configured to be disposed within a lumen of an intermediate tubular member. The inner tubular member 202 may extend from a proximal end disposed within a handle assembly to a distal end region 204. In some embodiments, a flared distal portion or funnel 206 may be formed as a separate component and coupled to the distal end region 204 of the inner tubular member 202. In other embodiments, the funnel 206 may be formed as an integral structure with the inner tubular member 202. While not explicitly shown the distal end region 204 and the funnel 206 may extend into the distal holding section. The funnel 206 may be capable of engaging the device 10 and the inner tubular member 202 may be used to "push" the device 10 out from distal holding section so as to deploy and anchor device 10 within a target region (e.g., a region of the heart such as the right ventricle).

Figure 6B:
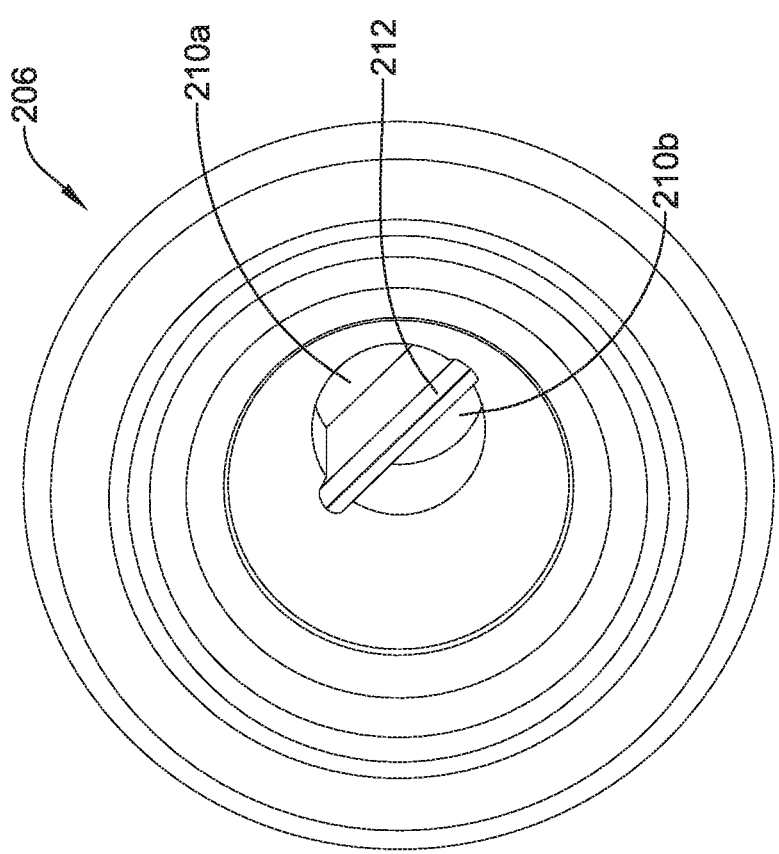
FIG. 6B is a perspective view of an illustrative bilumen funnel.

The inner tubular member 202 may have a lumen 208 extending from the proximal end to the distal end region 204 and through the funnel 206. The funnel 206 may include a wall 212 extending between outer walls of the funnel 206 and configured to bifurcate the lumen 208 into a bilumen having a first lumen 210a and a second lumen 210b, which can be seen more clearly in FIG. 6B which illustrates a perspective view of the funnel 206. Referring again, to FIG. 6A, the wall 212 may extend distally into the flared portion of the funnel 206 and/or proximally into the distal end region 204 of the inner tubular member 202, as desired. It is contemplated that the wall 212 may extend along any length of the lumen 208 desired. However, in some cases, increasing the length of the wall 212 may hinder flushing of the lumen 208 as the cross-sectional area of the lumen 208 becomes smaller. As shown in FIG. 6A, the wall 212, providing the bilumens 210a, 210b through the funnel 206, may only extend within the funnel 206, such that the inner tubular member 202 may have a single lumen 208. Thus, the lumen 208 through the inner tubular member 202 may be in fluid communication with both of the lumens 210a, 210b of the funnel 206. The funnel 206, the wall 212, and/or the inner tubular member 202 may be formed using any number of techniques, including, but not limited to, molding or extrusion. While the lumen 208 is described as being bifurcated into a bilumen, it is contemplated that the lumen 208 may be divided with any number of walls in a number of different configurations to divide the lumen 208 into as many lumens as desired, including, but not limited to, three, four, five, or more.

A tether 214 or other retaining feature may be used to releasably secure the device 10 to the delivery device 200. In some instances, the tether 214 may be a single or unitary length of material that may extend from a proximal end of the lumen 208, through the funnel 206, through the opening 38 of the device 10 and return to the proximal end of the inner tubular member 202 through the lumen 208 such that both ends of the tether 214 are positioned adjacent to the third hub portion of the handle assembly. In some instances, the ends of the tether 214 may be secured within a locking feature in the third hub portion.

The tether 214 may be assembled with the implantable device 10 and the delivery device 200 such that a portion of the tether 214a passes through the first lumen 210a of the bifurcated portion of the lumen 208 and a second portion of the tether 214b passes through the second lumen 210b of the bifurcated portion of the lumen 208. The wall 212 may extend across the width of the lumen 208 such that the first and second lumens 210a, 210b are isolated from one another along a length of the wall 212 (see, for example, FIG. 6B). The wall 212 (and the first and second lumens 210a, 210b) may hold the tether 214 in a spaced relationship adjacent the distal end region 204 of the inner tubular member 202 which may reduce and/or minimize twisting and/or tangling of the tether 214.

The tether 214 may be assembled with the implantable device 10 and the delivery device 200 using a number of different techniques. In one embodiment, a free end of the tether 214 may be passed through the opening 38 of the device 10. A vacuum may then be used to pull one or both free ends of the tether 214 through the lumen 208 of the inner tubular member 202 to the proximal end of the inner tubular member 202 where the free ends of the tether 214 can be secured within the handle assembly. It is contemplated that a free end may be positioned in each of the lumens 210a, 210b of the bifurcated portion of the lumen 208 such a portion of the tether 214 is disposed within each lumen 210a, 210b after assembly. In another embodiment, a stylet or a pull wire may be used to assemble the tether with the implantable device 10 and the delivery device 200. For example, a stylet or pull wire may be used to guide a free end of the tether 214 through a first lumen 210a of the bifurcated portion of the lumen 208, then through the opening 38 in the device 10, and then back through the second lumen 210b of the bifurcated portion of the lumen 208. The free end may then be pulled proximally through the lumen 208 to the handle assembly. It is contemplated that the second free end (e.g., the end not being advanced through the distal portion of the delivery device 200) may remain near the proximal end of the delivery device 200. Once the first free end has been advanced to the proximal end of the delivery device, both free ends can be secured within the handle assembly. These are just examples. It is contemplated that the tether 214 may be assembled with the implantable device 10 and the delivery device 200 in any manner desired.

Figure 7:
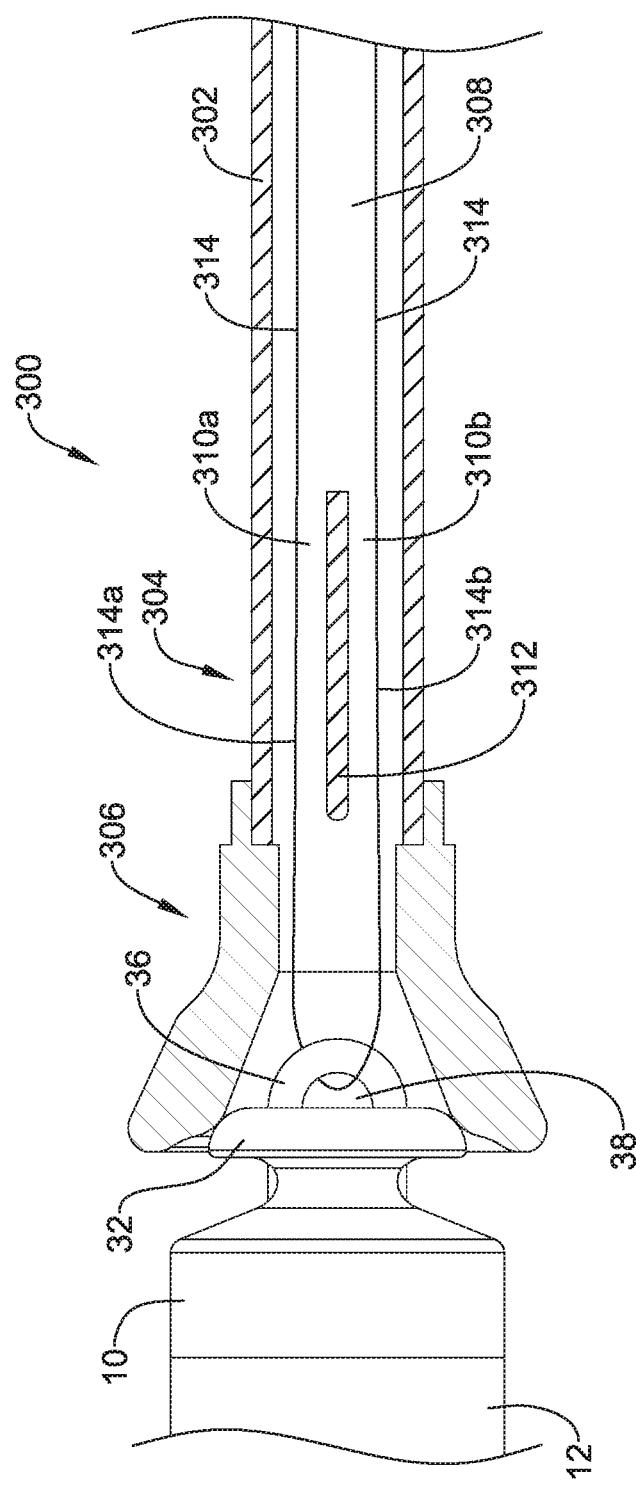
FIG. 7 is a partial cross-sectional side view of the distal portion of an alternative delivery device.

FIG. 7 is a partial cross-section of a distal portion of another alternative delivery device 300. The delivery device 300 may be similar in form and function to the delivery device 100 described above. However, for clarity some portions of the delivery device 300 are not illustrated including, but not limited to the outer tubular member, the intermediate tubular member, the distal holding section, and the handle assembly. It should be understood that while not shown these components may be present in the delivery device 300 and substantially the same as those described with respect to FIGS. 4 and 5.

The delivery device 300 may include an inner tubular member 302 configured to be disposed within a lumen of an intermediate tubular member. The inner tubular member 302 may extend from a proximal end disposed within a handle assembly to a distal end region 304. In some embodiments, a flared distal portion or funnel 306 may be formed as a separate component and coupled to the distal end region 304 of the inner tubular member 302. In other embodiments, the funnel 306 may be formed as an integral structure with the inner tubular member 302. While not explicitly shown the distal end region 304 and the funnel 306 may extend into distal holding section. The funnel 306 may be capable of engaging the device 10, and the inner tubular member 302 may be used to "push" the device 10 out from distal holding section so as to deploy and anchor device 10 within a target region (e.g., a region of the heart such as the right ventricle).

The inner tubular member 302 may have a lumen 308 extending from the proximal end to the distal end region 304 and through the funnel 306. The distal end region 304 of the inner tubular member 302 may include a wall 312 configured to bifurcate the lumen 308 into a bilumen having a first lumen 310a and a second lumen 310b along a portion thereof. The wall 312 may extend across the width of lumen 308. In some embodiments, the wall 312 may extend distally into the funnel 306 and/or further proximally within the inner tubular member, although this is not required. It is contemplated that the wall 312 may extend along any length of the lumen 308 desired. As shown in FIG. 7, the wall 312, providing the bilumens 310a, 310b, may only extend within a distal end region of the inner tubular member 302, such that a proximal portion of the inner tubular member 302 extending proximally therefrom may have a single lumen 308. Thus, the lumen 308 through the proximal portion of the inner tubular member 302 may be in fluid communication with both of the lumens 310a, 310b of the distal end region. The inner tubular member 302, the wall 312, and/or the funnel 306 may be formed using any number of techniques, including, but not limited to molding or extrusion. While the lumen 308 is described as being bifurcated into a bilumen, it is contemplated that the lumen 308 may be divided with any number of walls in a number of different configurations to divide the lumen 308 into as many lumens as desired, including, but not limited to three, four, five, or more.

A tether 314 or other retaining feature may be used to releasably secure the device 10 to the delivery device 300. In some instances, the tether 314 may be a single or unitary length of material that may extend from a proximal end of the lumen 308, through the funnel 306, through the opening 38 of the device 10 and return to the proximal end of the inner tubular member 302 through the lumen 308 such that both ends of the tether 314 are positioned adjacent to the third hub portion of the handle assembly. In some instances, the ends of the tether 314 may be secured within a locking feature in the third hub portion.

The tether 314 may be assembled with the implantable device 10 and the delivery device 300 such that a portion of the tether 314a passes through the first lumen 310a of the bifurcated portion of the lumen 308 and a second portion of the tether 314b passes through the second lumen 310b of the bifurcated portion of the lumen 308. The wall 312 may extend across the width of the lumen 308 such that the first and second lumens 310a, 310b are isolated from one another along a length of the wall 312. The wall 312 (and the first and second lumens 310a, 310b) may hold the tether 314 in a spaced relationship adjacent the distal end region 304 of the inner tubular member 302 which may reduce and/or minimize twisting and/or tangling of the tether 314.

The tether 314 may be assembled with the implantable device 10 and the delivery device 300 using a number of different techniques. In one embodiment, a free end of the tether 314 may be passed through the opening 38 of the device 10. A vacuum may then be used to pull both free ends of the tether 314 through the lumen 308 of the inner tubular member 302 to the proximal end of the inner tubular member 302 where the free ends of the tether 314 can be secured within the handle assembly. It is contemplated that a free end may be positioned in each of the lumens 310a, 310b of the bifurcated portion of the lumen 308 such a portion of the tether 314 is disposed within each lumen 310a, 310b after assembly. In another embodiment, a stylet or a pull wire may be used to assemble the tether with the implantable device 10 and the delivery device 300. For example, a stylet or pull wire may be used to guide a free end of the tether 314 through a first lumen 310a of the bifurcated portion of the lumen 308, then through the opening 38 in the device 10, and then back through the second lumen 310b of the bifurcated portion of the lumen 308. The free end may then be pulled proximally through the lumen 308 to the handle assembly. It is contemplated that the second free end (e.g., the end not being advanced through the distal portion of the delivery device 300) may remain near the proximal end of the delivery device 300. Once the first free end has been advanced to the proximal end of the delivery device, both free ends can be secured within the handle assembly. These are just examples. It is contemplated that the tether 314 may be assembled with the implantable device 10 and the delivery device 300 in any manner desired.

Figure 8:
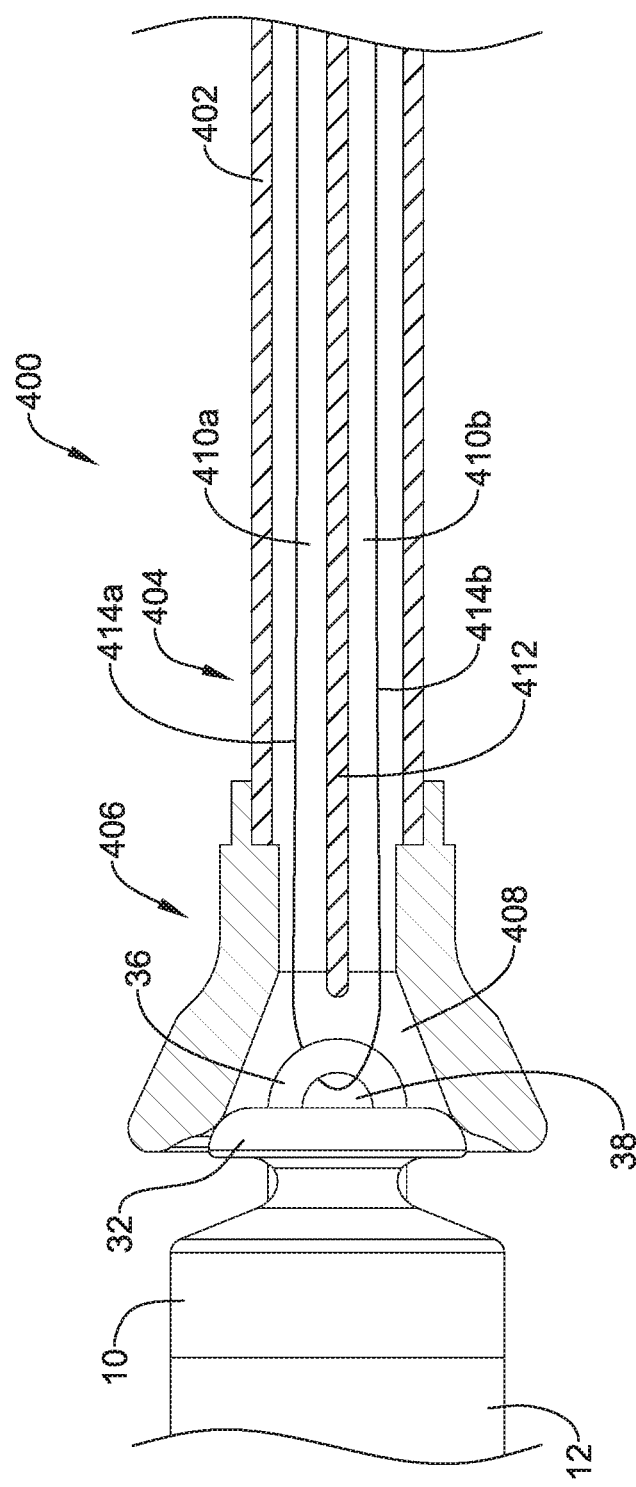
FIG. 8 is a partial cross-sectional side view of the distal portion of an alternative delivery device.

FIG. 8 is a partial cross-section of a distal portion of another alternative delivery device 400. The delivery device 400 may be similar in form and function to the delivery device 100 described above. However, for clarity some portions of the delivery device 400 are not illustrated including, but not limited to the outer tubular member, the intermediate tubular member, the distal holding section, and the handle assembly. It should be understood that while not shown these components may be present in the delivery device 400 and substantially the same as those described with respect to FIGS. 4 and 5.

The delivery device 400 may include an inner tubular member 402 configured to be disposed within a lumen of an intermediate tubular member. The inner tubular member 402 may extend from a proximal end disposed within a handle assembly to a distal end region 404. In some embodiments, a flared distal portion or funnel 406 may be formed as a separate component and coupled to the distal end region 404 of the inner tubular member 402. In other embodiments, the funnel 406 may be formed as an integral structure with the inner tubular member 402. While not explicitly shown, the distal end region 404 and the funnel 406 may extend into distal holding section. The funnel 406 may be capable of engaging the device 10, and the inner tubular member 402 may be used to "push" the device 10 out from distal holding section so as to deploy and anchor device 10 within a target region (e.g., a region of the heart such as the right ventricle).

The inner tubular member 402 may have a lumen 408 extending from the proximal end to the distal end region 404 and through the funnel 406. The inner tubular member 402 may include a wall 412 configured to bifurcate the lumen 408 into a bilumen having a first lumen 410a and a second lumen 410b along substantially an entire length thereof (e.g., from a proximal end to a distal end). The wall 412 may extend across the width of lumen 408. In some embodiments, the wall 412 may extend distally into the funnel 406, although this is not required. In other embodiments, the wall 412 may end proximal to the funnel 406. It is contemplated that the wall 412 may extend along any length of the lumen 408 desired. The inner tubular member 402, the wall 412, and/or the funnel 406 may be formed using any number of techniques, including, but not limited to molding or extrusion. While the lumen 408 is described as being bifurcated into a bilumen, it is contemplated that the lumen 408 may be divided with any number of walls in a number of different configurations to divide the lumen 408 into as many lumens as desired, including, but not limited to three, four, five, or more.

A tether 414 or other retaining feature may be used to releasably secure the device 10 to the delivery device 400. In some instances, the tether 414 may be a single or unitary length of material that may extend from a proximal end of the lumen 408, through the funnel 406, through the opening 38 of the device 10 and return to the proximal end of the inner tubular member 402 through the lumen 408 such that both ends of the tether 414 are positioned adjacent to the third hub portion of the handle assembly. In some instances, the ends of the tether 414 may be secured within a locking feature in the third hub portion.

The tether 414 may be assembled with the implantable device 10 and the delivery device 400 such that a portion of the tether 414a passes through the first lumen 410a of the bifurcated portion of the lumen 408 and a second portion of the tether 414b passes through the second lumen 410b of the bifurcated portion of the lumen 408. The wall 412 may extend across the width of the lumen 408 such that the first and second lumens 410a, 410b are isolated from one another along a length of the wall 412. The wall 412 (and the first and second lumens 410a, 410b) may hold the tether 414 in a spaced relationship along a length of the wall 412 which may reduce and/or minimize twisting and/or tangling of the tether 414.

The tether 414 may be assembled with the implantable device 10 and the delivery device 400 using a number of different techniques. In one embodiment, a free end of the tether 414 may be passed through the opening 38 of the device 10. A vacuum may then be used to pull both free ends of the tether 414 through the lumen 408 of the inner tubular member 402 to the proximal end of the inner tubular member 402 where the free ends of the tether 414 can be secured within the handle assembly. It is contemplated that a free end may be positioned in each of the lumens 410a, 410b of the bifurcated portion of the lumen 408 such a portion of the tether 414 is disposed within each lumen 410a, 410b after assembly. In another embodiment, a stylet or a pull wire may be used to assemble the tether with the implantable device 10 and the delivery device 400. For example, a stylet or pull wire may be used to guide a free end of the tether 414 through a first lumen 410a of the bifurcated portion of the lumen 408, then through the opening 38 in the device 10, and then back through the second lumen 410b of the bifurcated portion of the lumen 408. The free end may then be pulled proximally through the lumen 408 to the handle assembly. It is contemplated that the second free end (e.g., the end not being advanced through the distal portion of the delivery device 400) may remain near the proximal end of the delivery device 400. Once the first free end has been advanced to the proximal end of the delivery device, both free ends can be secured within the handle assembly. These are just examples. It is contemplated that the tether 414 may be assembled with the implantable device 10 and the delivery device 400 in any manner desired.

Figure 9:
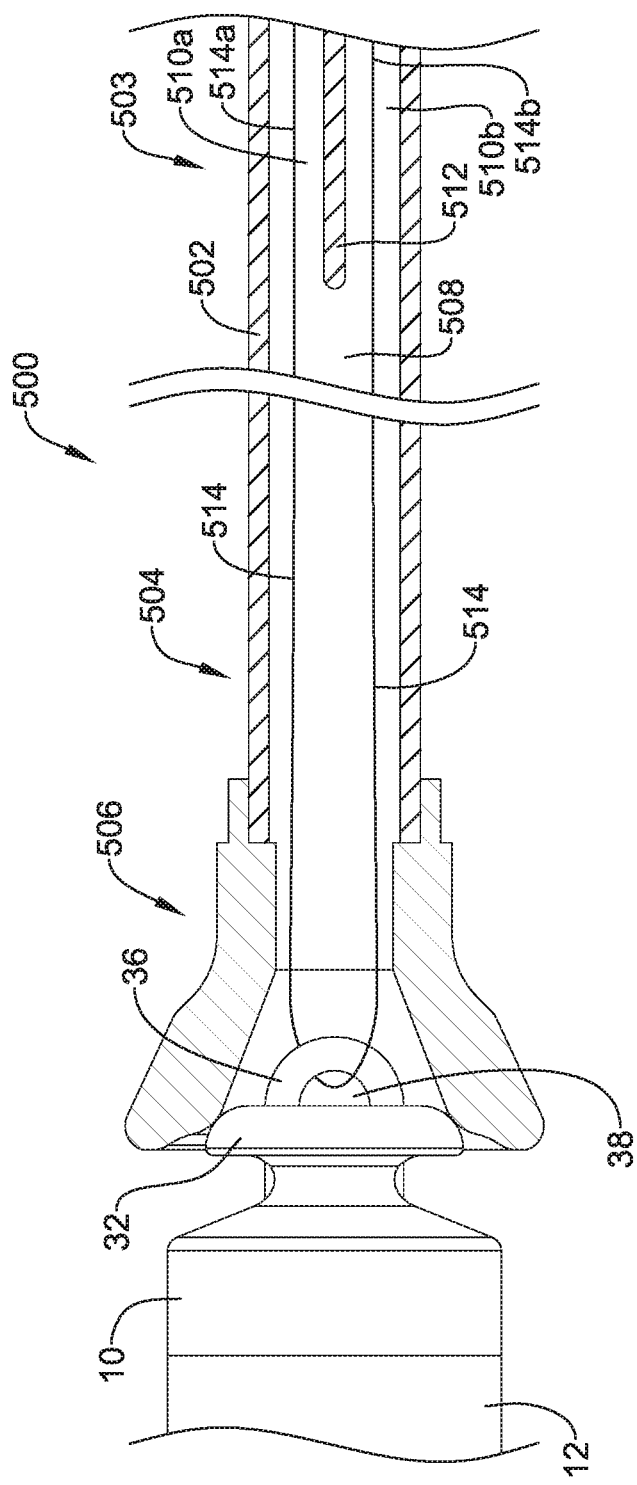
FIG. 9 is a partial cross-sectional side view of the distal portion and the proximal portion of an alternative delivery device.

FIG. 9 is a partial cross-section of a distal portion and proximal portion of another alternative delivery device 500. The delivery device 500 may be similar in form and function to the delivery device 100 described above. However, for clarity some portions of the delivery device 500 are not illustrated including, but not limited to the outer tubular member, the intermediate tubular member, the distal holding section, and the handle assembly. It should be understood that while not shown these components may be present in the delivery device 500 and substantially the same as those described with respect to FIGS. 4 and 5.

The delivery device 500 may include an inner tubular member 502 configured to be disposed within a lumen of an intermediate tubular member. The inner tubular member 502 may extend from a proximal end portion 503 disposed within a handle assembly to a distal end region 504. In some embodiments, a flared distal portion or funnel 506 may be formed as a separate component and coupled to the distal end region 504 of the inner tubular member 502. In other embodiments, the funnel 506 may be formed as an integral structure with the inner tubular member 502. While not explicitly shown, the distal end region 504 and the funnel 506 may extend into distal holding section. The funnel 506 may be capable of engaging the device 10, and the inner tubular member 502 may be used to "push" the device 10 out from distal holding section so as to deploy and anchor device 10 within a target region (e.g., a region of the heart such as the right ventricle).

The inner tubular member 502 may have a lumen 508 extending from the proximal end portion 503 to the distal end region 504 and through the funnel 506. The inner tubular member 502 may include a wall 512 configured to bifurcate the lumen 508 into a bilumen having a first lumen 510a and a second lumen 510b along a length adjacent the proximal portion 503 thereof. The wall 512 may extend across the width of lumen 508. It is contemplated that the wall 512 may extend along any length of the inner tubular member 502, desired. For example, the wall 512 may extend from the proximal end, or adjacent to the proximal end of the inner tubular member 502 distally to any point along the length of the lumen 508 desired. It is further completed that the wall 512 may be positioned at a location intermediate to the proximal end portion 503 and the distal end portion 504 and extend for any length of the lumen 508, as desired. As shown in FIG. 9, the wall 512, providing the bilumens 510a, 510b, may only extend within a proximal end region of the inner tubular member 502, such that a distal portion of the inner tubular member 502 extending distally therefrom may have a single lumen 508. Thus, the lumen 508 through the distal portion of the inner tubular member 502 may be in fluid communication with both of the lumens 510a, 510b of the proximal end region. The inner tubular member 502, the wall 512, and/or the funnel 506 may be formed using any number of techniques, including, but not limited to molding or extrusion. While the lumen 508 is described as being bifurcated into a bilumen, it is contemplated that the lumen 508 may be divided with any number of walls in a number of different configurations to divide the lumen 508 into as many lumens as desired, including, but not limited to three, four, five, or more.

A tether 514 or other retaining feature may be used to releasably secure the device 10 to the delivery device 500. In some instances, the tether 514 may be a single or unitary length of material that may extend from a proximal end of the lumen 508, through the funnel 506, through the opening 38 of the device 10 and return to the proximal end of the inner tubular member 502 through the lumen 508 such that both ends of the tether 514 are positioned adjacent to the third hub portion of the handle assembly. In some instances, the ends of the tether 514 may be secured within a locking feature in the third hub portion.

The tether 514 may be assembled with the implantable device 10 and the delivery device 500 such that a portion of the tether 514a passes through the first lumen 510a of the bifurcated portion of the lumen 508 and a second portion of the tether 514b passes through the second lumen 510b of the bifurcated portion of the lumen 508. The wall 512 may extend across the width of the lumen 508 such that the first and second lumens 510a, 510b are isolated from one another along a length of the wall 512. The wall 512 (and the first and second lumens 510a, 510b) may hold the tether 514 in a spaced relationship along a length of the wall 512 which may reduce and/or minimize twisting and/or tangling of the tether 514.

The tether 514 may be assembled with the implantable device 10 and the delivery device 500 using a number of different techniques. In one embodiment, a free end of the tether 514 may be passed through the opening 38 of the device 10. A vacuum may then be used to pull both free ends of the tether 514 through the lumen 508 of the inner tubular member 502 to the proximal end of the inner tubular member 502 where the free ends of the tether 514 can be secured within the handle assembly. It is contemplated that a free end may be positioned in each of the lumens 510a, 510b of the bifurcated portion of the lumen 508 such a portion of the tether 514 is disposed within each lumen 510a, 510b after assembly. In another embodiment, a stylet or a pull wire may be used to assemble the tether with the implantable device 10 and the delivery device 500. For example, a stylet or pull wire may be used to guide a free end of the tether 514 through a first lumen 510a of the bifurcated portion of the lumen 508, then through the opening 38 in the device 10, and then back through the second lumen 510b of the bifurcated portion of the lumen 508. The free end may then be pulled proximally through the lumen 508 to the handle assembly. It is contemplated that the second free end (e.g., the end not being advanced through the distal portion of the delivery device 500) may remain near the proximal end of the delivery device 500. Once the first free end has been advanced to the proximal end of the delivery device, both free ends can be secured within the handle assembly. These are just examples. It is contemplated that the tether 514 may be assembled with the implantable device 10 and the delivery device 500 in any manner desired.

In any of the above embodiments, the device 10 may still be affixed to the delivery device 100, 200, 300, 400, 500 through the tether 112, 212, 312, 412, 512. Once the clinician has verified the position of the device 10, the fixation of the device 10 and/or the electrical performance of the device 10, the tether 112, 212, 312, 412, 512 may be removed. It is contemplated that the fixation of the device 10

(e.g., how well the hooks 26 are secured to the heart tissue) may be tested by gently tugging on the ends of the tether 112, 212, 312, 412, 512. The tether 112, 212, 312, 412, 512 may be removed by unlocking the tether lock 164 (see, for example, FIG. 4), removing the tether cap 166 (see, for example, FIG. 4), cutting the tether 112, 212, 312, 412, 512 at some location along its length, and pulling on one of the ends until the opposite end has passed through the opening 38 of the device 10 such that the device 10 is free from the tether 112, 212, 312, 412, 512. The tether cap 166 may include a means to separate the tether strands, including but not limited to, bifurcated lumens, clamping mechanisms, etc.

It is contemplated that the bifurcation of the lumen 208, 308, 408, 508 of the inner tubular member 208, 308, 408, 508 may facilitate removal of the tether 212, 312, 412, 512 by reducing or minimizing twisting or tangling of the tether 212, 312, 412, 512. For example, reducing the twisting or tangling of the tether 212, 312, 412, 512 may reduce the force required to disengage the tether 212, 312, 412, 512 from the implantable device 10. In some instances, the tether 112 may be affixed to a portion of the tether cap 166 (e.g., creating a loop) such that the tether 112 must be cut to allow the device 10 to be freed from the tether 112.

The materials that can be used for the various components of the delivery devices, such as delivery device 100, 200, 300, 400, 500 (and/or other delivery structures disclosed herein) and the various members disclosed herein may include those commonly associated with medical devices. For simplicity purposes, the following discussion makes reference the delivery device 100, 200, 300, 400, 500 and components of thereof. However, this is not intended to limit the devices and methods described herein, as the discussion may be applied to other similar delivery systems and/or components of delivery systems or devices disclosed herein.

The delivery device 100, 200, 300, 400, 500 and/or other components of delivery system may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the polymer can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

In at least some embodiments, portions or all of the delivery device 100, 200, 300, 400, 500 and/or other components of delivery system may be doped with, made of, or otherwise include a radiopaque material. Radiopaque materials are understood to be materials capable of producing a relatively bright image on a fluoroscopy screen or another imaging technique during a medical procedure. This relatively bright image aids the user of the delivery device 100 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the delivery device 100 to achieve the same result.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A delivery device for delivering an implantable leadless pacing device, the delivery device comprising:
   a tubular member including a lumen extending from a proximal end to a distal end thereof, the tubular member including a distal holding section defining a cavity therein having an implantable leadless pacing device disposed therein; and
   an inner member including a lumen extending from a proximal end to a distal end thereof, the inner member slidably disposed within the lumen of the tubular member;

a funnel coupled to the distal end of the inner tubular member, the lumen of the inner tubular member extending through the funnel;

a handle assembly including a first hub secured to the proximal end of the tubular member and a second hub secured to the proximal end of the inner member, wherein actuation of the first hub relative to the second hub imparts relative longitudinal movement between the tubular member and the inner member;

wherein at least a portion of the lumen of the inner member is bifurcated to form a first lumen and a second lumen, the first lumen configured to receive a first portion of a tether and the second lumen configured to receive a second portion of the tether, wherein the first and second lumens extend along less than an entire length of the lumen of the inner tubular member and are positioned within the funnel;

a tether extending through an opening of the implantable leadless pacing device such that a first portion of the tether extends proximally from the opening and passes freely through the first lumen to the handle assembly and a second portion of the tether extends proximally from the opening and passes freely through the second lumen to the handle assembly, the first portion of the tether extending alongside the second portion of the tether;

wherein a proximal end of the first portion of the tether and a proximal end of the second portion of the tether are both secured within the handle assembly.

2. The delivery device of claim 1, wherein the first portion of the tether extending proximal of the first lumen has an outer diameter along its length that is less than a cross-sectional width of the first lumen, and the second portion of the tether extending proximal of the second lumen has an outer diameter along its length that is less than a cross-sectional width of the second lumen.

3. The delivery device of claim 1, wherein an entire length of the tether moves axially freely through an entirety of the first and second lumens.

4. A delivery device for delivering an implantable leadless pacing device, the delivery device comprising:

a tubular member including a lumen extending from a proximal end to a distal end thereof, the tubular member including a distal holding section defining a cavity therein having an implantable leadless pacing device disposed therein;

an inner member including a lumen extending from a proximal end to a distal end thereof, the inner member slidably disposed within the lumen of the tubular member;

a funnel coupled to the distal end of the inner member, the lumen of the inner member extending through the funnel;

a handle assembly coupled to the proximal end of the tubular member and the proximal end of the inner member;

wherein at least a portion of a length of the lumen of the inner member is bifurcated into a first lumen and a second lumen, wherein the first and second lumens are positioned within the funnel; and a tether extending through an opening of the implantable leadless pacing device such that a first portion of the tether extends proximally from the opening and passes freely through the first lumen to the handle assembly and a second portion of the tether extends proximally from the opening and passes freely through the second lumen to the handle assembly, the first portion of the tether extending alongside the second portion of the tether;

wherein a proximal end of the first portion of the tether and a proximal end of the second portion of the tether are both secured within the handle assembly.

5. The delivery device of claim 4, wherein the first portion of the tether extending proximal of the first lumen has an outer diameter along its length that is less than a cross-sectional width of the first lumen, and the second portion of the tether extending proximal of the second lumen has an outer diameter along its length that is less than a cross-sectional width of the second lumen.

6. The delivery device of claim 4, wherein an entire length of the tether moves axially freely through an entirety of the first and second lumens.

* * * * *